US006966650B2

(12) United States Patent
Hu et al.

(10) Patent No.: US 6,966,650 B2
(45) Date of Patent: Nov. 22, 2005

(54) METHOD AND APPARATUS FOR AN AUTOMATED PROCEDURE TO DETECT AND MONITOR EARLY-STAGE GLAUCOMA

(76) Inventors: Zongqi Hu, 106 Anderson St., Raritan, NJ (US) 08869; Vance Marc Zemon, 30 East St., West Nyack, NY (US) 10994

( * ) Notice: Subject to any disclaimer, the term of this patent is extended or adjusted under 35 U.S.C. 154(b) by 140 days.

(21) Appl. No.: 10/608,627

(22) Filed: Jun. 27, 2003

(65) Prior Publication Data

US 2004/0263780 A1 Dec. 30, 2004

(51) Int. Cl.$^7$ .............................. A61B 3/00; A61B 3/10; A61B 5/05; A61B 13/00
(52) U.S. Cl. ..................... 351/205; 351/246; 600/544; 600/558
(58) Field of Search .................. 351/205, 211, 221, 351/222, 237, 246; 600/544, 545, 558

(56) References Cited

U.S. PATENT DOCUMENTS

| | | | |
|---|---|---|---|
| 4,634,243 A | 1/1987 | Massof et al. ............... | 351/243 |
| 5,065,767 A | 11/1991 | Maddess ..................... | 128/745 |
| 5,176,147 A | 1/1993 | Bodis-Wollner ............ | 128/745 |
| 5,539,482 A | 7/1996 | James et al. ................. | 351/246 |
| 5,912,723 A | 6/1999 | Maddess ..................... | 351/246 |
| 6,477,407 B1 | 11/2002 | Klistorner et al. .......... | 600/544 |
| 6,527,391 B1 | 3/2003 | Heijl et al. .................. | 351/243 |
| 6,688,746 B2 * | 2/2004 | Malov ......................... | 351/239 |

OTHER PUBLICATIONS

"Visual Evoked Potential Assessment Of The Effects Of Glaucoma On Visual Subsystems," Vision Research 38 (1998) pp. 1901-1911. Vivienne C. Greenstein, Steven Seliger, Vance Zemon, Robert Ritch.

Multifocal VEP and ganglion cell damage: Applications and limitations for the study of Glaucoma. Progres in Retinal and Eye Research, 22, pp. 201-251. Hood, D.C. & Greenstein,. V.C. (2003).

Badr, A.A., Zemon, V.M., Greenstein, V.C., Clemens, C.J., Holopigian, K, Seiple, W.: M-versus P-Function: Releationship to visual field loss in patients with open angel glaucoma. Investigative Ophthalmology and Visual Science, 2001, 42/4. S787.

Benoff, K.; Fitzerald; K. Zemon, V. Pinkhasov, E., Gordon, J., Cibis, G.: Magnocelluar ON-pathway deficits in Duchenne Muscular Dystrophy: A visual evoked potential study. Investigative Ophthalmology and Visual Science, 2001, 424/4, S787.

Fitzgerald, K.M., Hartmann, E.E., Zemon, V.M.: Pattern VEPs to cotnrast-increment and -decrement stimuli in patients with Duchenne Muscular Dystrophy or Congenitally Stationary Night Blindness. Investigative Ophthalmology and Visual Science, 1994, 35/4, 2414.

(Continued)

Primary Examiner—Brian L. Casler
Assistant Examiner—John R. Sanders
(74) Attorney, Agent, or Firm—Walter J. Tencza, Jr.

(57) ABSTRACT

A system and a method for automated, electrophysiological assessment of visual function in glaucoma suspects and patients is provided using visual evoked potentials measured in response to periodic stimuli presented to the patients. The method may be comprised of the steps of entering a patient's information into a computer, initializing a visual stimulus for the patient, recording a plurality of visual evoked potential signals obtained from one or more electrodes attached to the patient's scalp, saving and processing digitized data relating to the visual evoked potential signals, and determining if the likelihood of glaucoma is high or low based on the data.

12 Claims, 4 Drawing Sheets

OTHER PUBLICATIONS

"A new statistic for steady-state evoked potentials," Jonathan D. Victor and Joelle Mast, Publication Jul. 6, 1990, New York, NY, pp. 378-388.

Hartline, H.K.: The response of single optic nerve fibers of the vertebrate eye to illumination of the retina. American Journal of Physiology, 1938, 121, 400-415.

Kaplan, E., Lee, B.B., Shapley, R.M.: New views of primate retinal function. In: Progress in Retinal Research (Osborne, N.N. & Chader, G.J., eds), 1990, 9, 273-336. New York: Pergamon Press. Schiller, P.H., Sandell, J.H. & Maunsell, J.H.R.: Functions of the ON and OFF channels of the visual system. Nature, 1986, 322, 824-825.

* cited by examiner

METHOD AND APPARATUS FOR AN AUTOMATED PROCEDURE TO DETECT AND MONITOR EARLY-STAGE GLAUCOMA

FIELD OF THE INVENTION

The present invention relates to the field of medical diagnosis and monitoring.

BACKGROUND OF THE INVENTION

Glaucoma (in particular, primary open-angle glaucoma) is one of the leading causes of blindness in the United States (Prevent Blindness America and the National Eye Institute, 2002). It produces a gradual and progressive degeneration of retinal ganglion cells, which transmit visual information along the optic nerve to the brain. Unfortunately, by the time this glaucomatous neuropathy is detected, there is typically extensive and permanent damage to the visual system and profound loss in visual function. There is evidence to indicate that select pathways of the visual system are affected in an early stage of the disease. Although glaucoma is often associated with elevated intraocular pressure, this is not always the case. Presently, there is a paucity of clinical screening and diagnostic tools available to vision professionals that aid in the early detection of this disease and in the monitoring of treatments for the purpose of neuroprotection.

The retina of the eye contains more than 130 million light-sensitive cells. These cells convert light into neural signals that are processed by a variety of neurons for certain features, and then transmitted via the optic nerve to the brain for interpretation. Birth defects, trauma from accidents, numerous kinds of disease, and age-related deterioration of the components of the eye can all contribute to visual disorders. Information processing in the brain is electrochemical in nature. Evoked potentials are the electrical responses of the brain elicited by sensory stimulation. The electrical responses of the brain produced by visual stimulation are visual evoked potentials. Alterations in the characteristic visual evoked potential indicate anomalies along the visual pathways.

Typically, the visual evoked potential (VEP) is measured from the scalp via surface electrodes while visual stimuli are displayed on a video monitor placed in front of the patient. When stimulation is applied to a particular sense of a human being, a corresponding brain potential is evoked at an information-processing part of the brain that functions to manage that particular sense. Visual evoked potentials can be used for diagnostic testing to assist physicians in the diagnosis of brain damage, diseases of the central nervous system, and diseases of the visual system in particular.

The visual evoked potential (VEP) is a noninvasive measure of cortical activity elicited by a visual stimulus. It is the sum of electrical signals conducted to the surface of the head and it is capable of providing quantitative information on the dynamics of the visual system. The manner in which the VEP is typically elicited, however, precludes the exploration of selective visual processes, and the manner in which the VEP is typically analyzed lacks efficiency and the rigor needed for its use as a pragmatic and objective tool. The subjectivity involved in the usual description of the VEP waveform has been a hindrance in all of its applications including the assessment of glaucoma. Thus, a potentially powerful tool for functional dissection of the visual pathways has been largely overlooked. Over the last several years, a number of stimulation and analysis techniques have been introduced to the field that provide the basis for an electrophysiological instrument that obviates these problems.

Hartline (1938) discovered the existence of ON and OFF cells in the visual system. ON and OFF cells originate at the first synapse in the retina, and they mediate the distinct perceptions of brightness (positive contrast) and darkness (negative contrast), respectively (Schiller, Sandell, & Maunsell, 1986). The ON pathway is particularly sensitive to disease processes involved in congenital stationary night blindness, muscular dystrophy, and glaucoma (Badr et al., 2003; Benoff et al., 2001; Fitzgerald et al., 1994; Greenstein et al., 1998).

Another important functional subdivision of the primary visual pathway was first discovered in the major relay station for visual processing in the brain, the lateral geniculate nucleus (LGN), but it too has its origin in the retina (Kaplan, Lee, & Shapley, 1990). The magnocellular (large cell) and parvocellular (small cell) layers of the LGN receive their inputs from M and P retinal ganglion cells, respectively. The morphological differences in these two types of cells produce quite different response characteristics. M cells are large in size and are highly sensitive to luminance contrast (respond to small differences in light level), whereas P cells are small in size and are relatively insensitive to luminance contrast. Both M and P pathways contain ON and OFF cells. Cells in the magnocellular and parvocellular layers of the LGN form synapses (make connections) in different sublayers of the primary visual cortex (the first visual processing center in posterior region of the brain), and synaptic activity occurring on parts of the neurons in this area is the principal source of the VEP. Evidence exists to indicate that the ON cells in the magnocellular pathway are particularly sensitive to and affected by disease processes such as muscular dystrophy (Benoff et al., 2001) and glaucoma (Greenstein et al., 1998; Badr et al., 2003).

Methods and systems exist for the detection of glaucoma using visual evoked responses (e.g., the multifocal VEP, Hood & Greenstein, 2003; behavioral measures obtained in visual field testing with conventional perimeters or frequency-doubling perimeters). However, the scientific principles, the stimuli used and the data processing methods in those techniques differ from the ones involved in the current invention.

Figure 3:
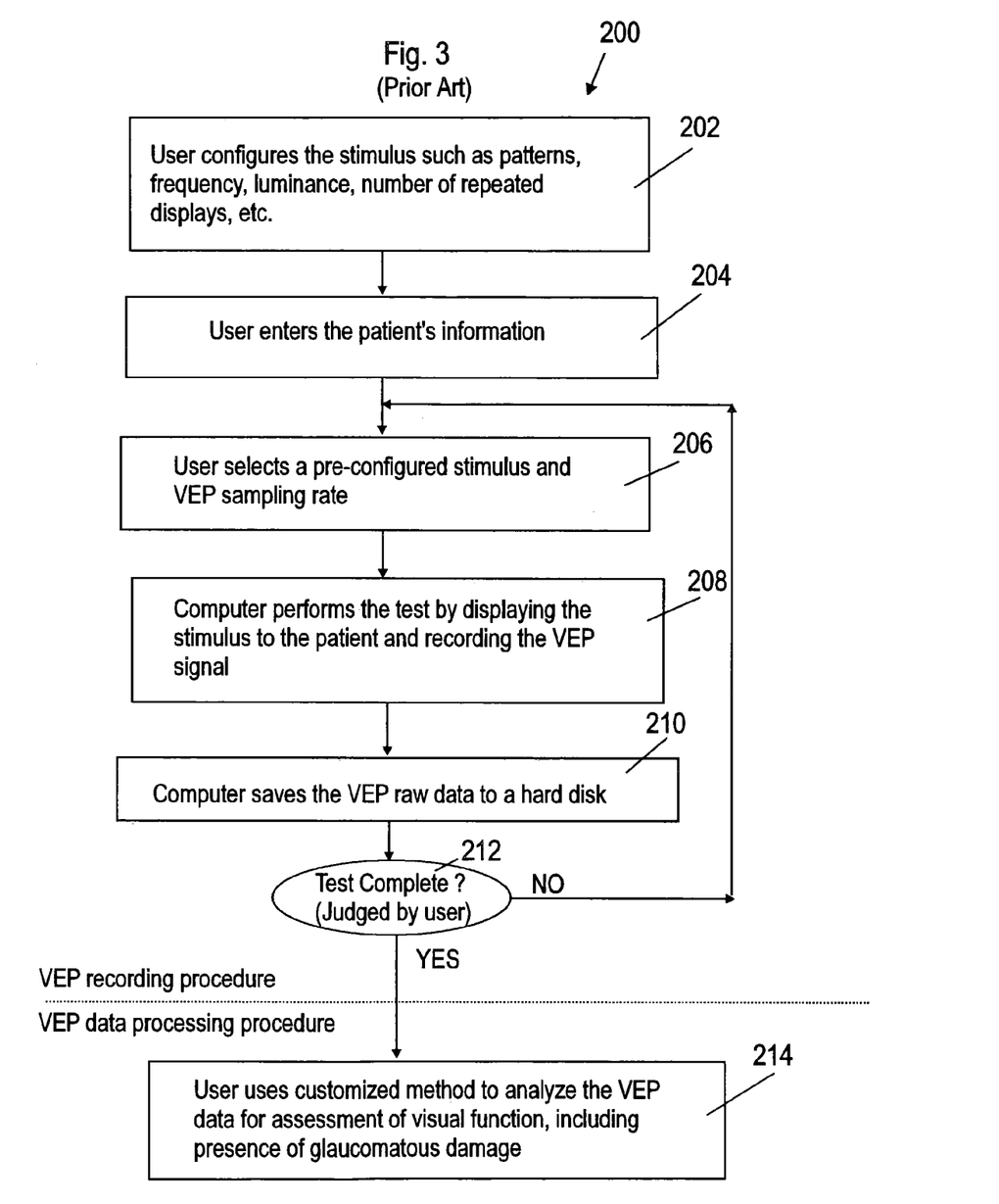
FIG. 3 shows a flow chart of a prior art procedure and method used to conduct studies on early-stage glaucoma.

In the prior art, a general VEP recording system was used in laboratories. The procedure of using this machine for visual neurophysiological studies is illustrated by flow chart 200 in FIG. 3. First at step 202, the user needs to configure the stimulus for parameters (e.g., spatial patterns, temporal frequency, contrast, luminance, number of repeated tests, etc.), and save the stimulus configuration in the system's computer. At step 204, a user enters the patient's information. Before starting the test, the user needs to select the pre-configured stimulus and the VEP data acquisition parameters (e.g., sampling rate in terms of the stimulus frequency and the frequency components in the VEP of interest to be extracted), at step 206. At step 208 the computer performs the test by displaying a stimulus to a patient and recording a VEP signal. At step 210 the computer saves VEP raw data to a hard disk. At step 212 the user has to determine if the test is complete. If the answer is no, the procedure goes back to step 206. If the answer is yes, then at step 214 (not automatically following step 212), the user has to take the stored VEP raw data and process the data with custom-made software to perform an assessment of visual function.

SUMMARY OF THE INVENTION

The present invention provides a system and method for automated, electrophysiological assessment of visual function in glaucoma suspects and patients using visual evoked potentials measured in response to periodic stimuli presented to the patients.

In the current system and method, a novel approach to stimulation and data processing are introduced to separate in a rapid and automated manner the contributions to the VEP response from the ON subdivision of the magnocellular pathway, which is sensitive to early-stage glaucomatous neuropathy (Greenstein et al., 1998). In a system in accordance with the present invention, the processed VEP result is compared with a preset critical value to indicate the likelihood of the patient's glaucoma status—high (positive) or low (negative) with a certain confidence level.

The present invention is directed to the design of a system and method for performing an automated neurophysiological test for the detection and monitoring of early-stage glaucoma. It includes the generation and display of a periodic visual stimulus, presented several times, for observation by a patient, and the measurement of the patient's visual evoked potential (VEP) in response to the visual stimulus. The VEP data, elicited by each stimulus displayed, is recorded and stored, and then processed with a digital Fourier transform (DFT) and analyzed with $T^2_{circle}$ statistical methods (Victor & Mast, 1991). The ratio of the mean amplitude value of the fundamental frequency component of the VEP (signal) to the noise estimated by the $T^2_{circle}$ statistic is calculated and compared with a critical value to yield a result—likelihood of glaucomatous neuropathy high (positive test result) or low (negative test result).

The method to compute the $T^2_{circle}$ statistic, previously described for an embodiment of the present invention, was not a part of general-purpose systems of the prior art. In the prior art, the Fourier components of VEP responses were needed to be processed further with the use of customized spreadsheets in standard, commercial software to derive estimates of noise and to compute signal-to-noise ratios. The prior art laboratory machine for detection and monitoring of glaucomatous neuropathy was laborious and not of practical value. Some of the differences of the prior art laboratory device in comparison with the current system of at least one embodiment of the present invention are the following:

The configuration of the stimulus, data collection, and data processing parameters is a complicated process in the prior art. It requires a significant learning period for a new user, and it relies heavily on a user's previous experience with the prior art machine and expertise in the VEP field. Thus, the test result depends greatly on the user.

Since the prior art system lacks complete data processing tools, though the system has built-in and pre-configured methods such as signal averaging and Fourier analysis, it doesn't provide the statistical methods required for glaucoma testing, which is necessary to generate a criterion to separate the normal and abnormal responses. Usually the user has to save the VEP data for further processing with other facilities. The required multiple processing steps significantly decrease convenience and increase time consumption.

The prior art system does not provide an objective measure. The user must perform extensive analysis on the raw data with custom-made software to yield a product that is interpretable. Thus, the prior art system is serviceable for only a handful of professionals with a high degree of specialized knowledge in this field.

The present invention in one embodiment provides a method comprising the steps of entering a patient's information into a computer, initializing a visual stimulus for the patient, recording a plurality of visual evoked potential signals obtained from one or more electrodes attached to the patient's scalp, saving data relating to the visual evoked potential signals, and determining if the likelihood of glaucoma is high or low based on the data. The method may further include performing a discrete Fourier transform on the saved data, performing a multivariate statistical method to determine a signal-to-noise ratio for the data, determining a critical signal-to-noise value, and comparing the signal-to-noise ratio with the critical value and determining if the likelihood of glaucoma is high or low based on the comparison. The method may also include displaying an indication of whether there is a high or low likelihood of glaucoma on a computer monitor. The multivariate statistical method applied may be a $T^2_{circle}$ method.

In one embodiment of the present invention an apparatus is provided comprising a computer processor and a computer memory. The computer processor may be programmed by computer software to receive a patient's information (e.g., ID number, gender, date of birth, etc.) initialize a visual stimulus for the patient, record a plurality of visual evoked potential signals obtained from one or more electrodes attached to the patient's scalp, save data relating to the visual evoked potential signals to the computer memory, and determine if a likelihood of glaucoma is high or low based on the data.

The computer processor may be programmed to perform a discrete Fourier transform on the saved data, perform a multivariate statistical computation to determine a signal-to-noise ratio for the data, and to compare the signal-to-noise ratio with a preset critical signal-to-noise value to determine if the likelihood of glaucoma is high or low based on the comparison.

The apparatus in at least one embodiment may be comprised of a computer monitor; wherein the computer processor may be programmed to display an indication of whether there is a high or low likelihood of glaucoma on the computer monitor.

The apparatus is also comprised of a VEP recording and measuring device that amplifies the VEP signals picked up by the surface electrodes and converts these analog signals to digital signals which are then fed into the computer processor.

DETAILED DESCRIPTION OF THE DRAWINGS

Figure 1:
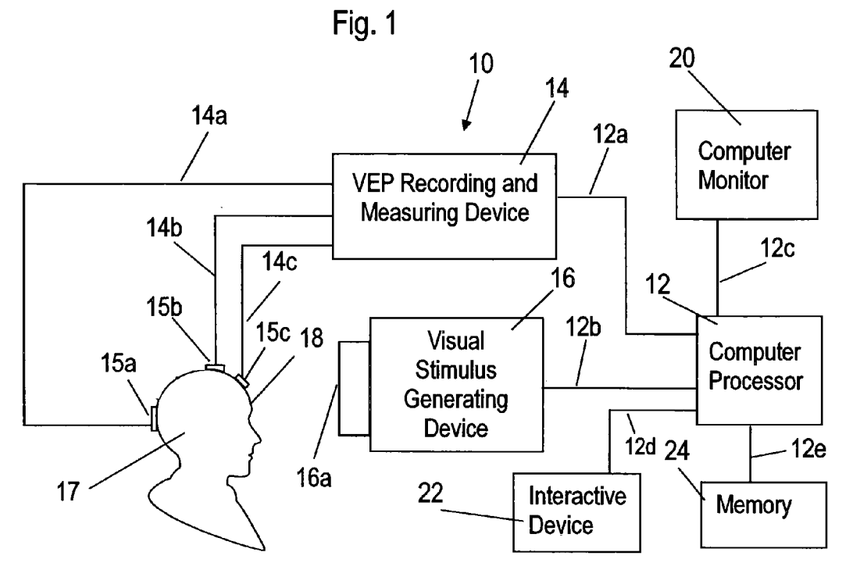
FIG. 1 is a block diagram illustrating the overall architecture of an embodiment of the present invention.

FIG. 1 is a block diagram of an apparatus 10 of an overall architecture of an embodiment of the present invention. The apparatus 10 includes a computer processor 12, a VEP recording and measuring device 14, a visual stimulus generating device 16, a computer monitor 20, an interactive device 22, and a memory 24. The interactive device 22 may be a computer mouse and/or a keyboard or other input device. The memory 24 may be any type of computer memory. The computer monitor 20 may be a typical computer display monitor.

The computer processor 12 is electrically connected by a communications bus (e.g., PCI (Peripheral Component Interconnect)) 12b to a visual stimulus generating device 16 and by a communications bus (e.g., PCI, USB (Universal Serial Bus), etc.) 12a to a VEP recording and measuring device 14. The VEP recording and measuring device 14 is electrically connected by communications lines 14a, 14b, and 14c to electrodes 15a, 15b, and 15c. The electrodes 15a, 15b, and 15c are attached to the head 18 of a person or patient 17. The computer processor 12 is electrically connected by communications lines 12c, 12d, and 12e, to the computer monitor 20, interactive device 22, and the memory 24, respectively.

The computer processor 12 may be a computer processor for a typical personal computer. The computer processor 12 typically controls the operation of both the VEP recording and measuring device 14 for data acquisition and the visual stimulus-generating device 16 for stimulus display.

The VEP recording and measuring device 14 typically includes an amplifier to enhance VEP signals being acquired via communications lines 14a, 14b, or 14c, and an A/D (analog to digital) converter to convert the VEP analog signals to digital signals which are sent via communications bus 12a to the computer processor 12 for processing. The amplifier of the VEP recording and measuring device 14 optically isolates patients, such as patient 17, from the electrical source, such as a power source for the device 14, for safety. As is known, the amplifier of device 14 has a high common mode rejection ratio, low noise and high stability for low VEP signal operation. The amplifier also has a band-pass filter to reject the low-frequency drift and high-frequency noise beyond the bandwidth.

The visual stimulus-generating device 16, typically includes a video display monitor and a graphics card, and is connected to and controlled by the computer processor 12, for generating visual stimuli on the display screen 16a to be viewed by patients, such as the patient 17 in FIG. 1.

The neural responses such as neural response from head 18 to the stimuli are picked up by the sensory electrodes 15a, 15b, and 15c, attached non-invasively to the patient's scalp 18 and are amplified, recorded and digitized in the VEP recording and measuring device 14 as is known in the art. The electrodes are positioned on the scalp 18 of the patient over the visual cortex (active electrode 15a to receive the VEP), the middle of the forehead (reference electrode 15c), and the right side of the forehead (floating ground electrode 15b). This arrangement of attachment of electrodes is known in the art. Electrodes 15a–15c are connected by communications lines 14a, 14b, and 14c, which are typically hardwires, to the VEP recording and measuring device 14. The interactive device 22 provides a means to input information to the computer 12 regarding the patient 17 being tested (e.g., ID number, gender, date of birth, etc.). The operator's computer monitor 20 displays the information entered via the interactive device 22, an operation menu for instruction selection, as well as test results as demonstrated in FIG. 5.

Figure 2:
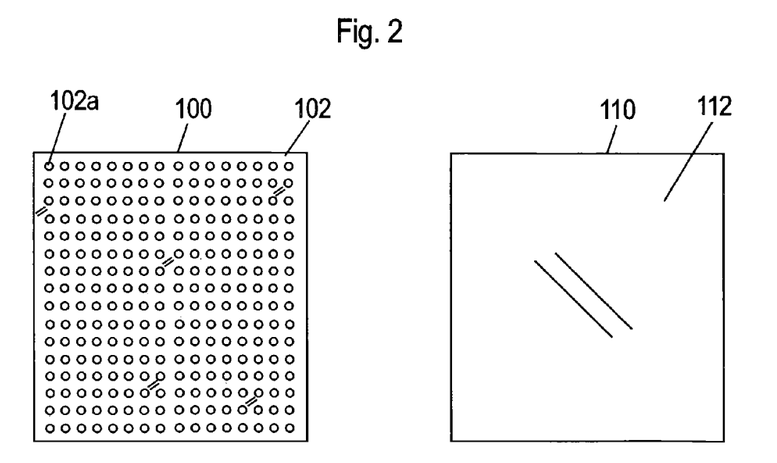
FIG. 2 illustrates an isolated-check stimulus and a uniform-field stimulus used in an embodiment of the present invention.

FIG. 2 illustrates an isolated-check pattern 100 and a uniform field 110. The pattern 100 and the field 110 may be displayed alternatively in a periodic manner at a frequency of approximately twelve Hertz by the visual stimulus-generating device 16. Typically there are 32×32 isolated-checks (squares) such as check 102a, which appear upon a steady background 102. The background luminance, such as for background 102 and background 112 for both pattern 100 and uniform field 110, respectively, is typically (known in the art) 100 nits (cd/m2). The luminance of the checks, such as, check 102a, is 8% higher than that of the background, such as background 102 (108 nits), which has been shown to be the critical stimulus condition for the detection of glaucomatous damage. Patients, such as patient 17 in FIG. 1, typically view a stimulus, such as either 100 or 110 in FIG. 2, with a physical image size of 20 cm (centimeters) ×20 cm (centimeters) at a distance of one hundred and fifteen centimeters.

Figure 4:
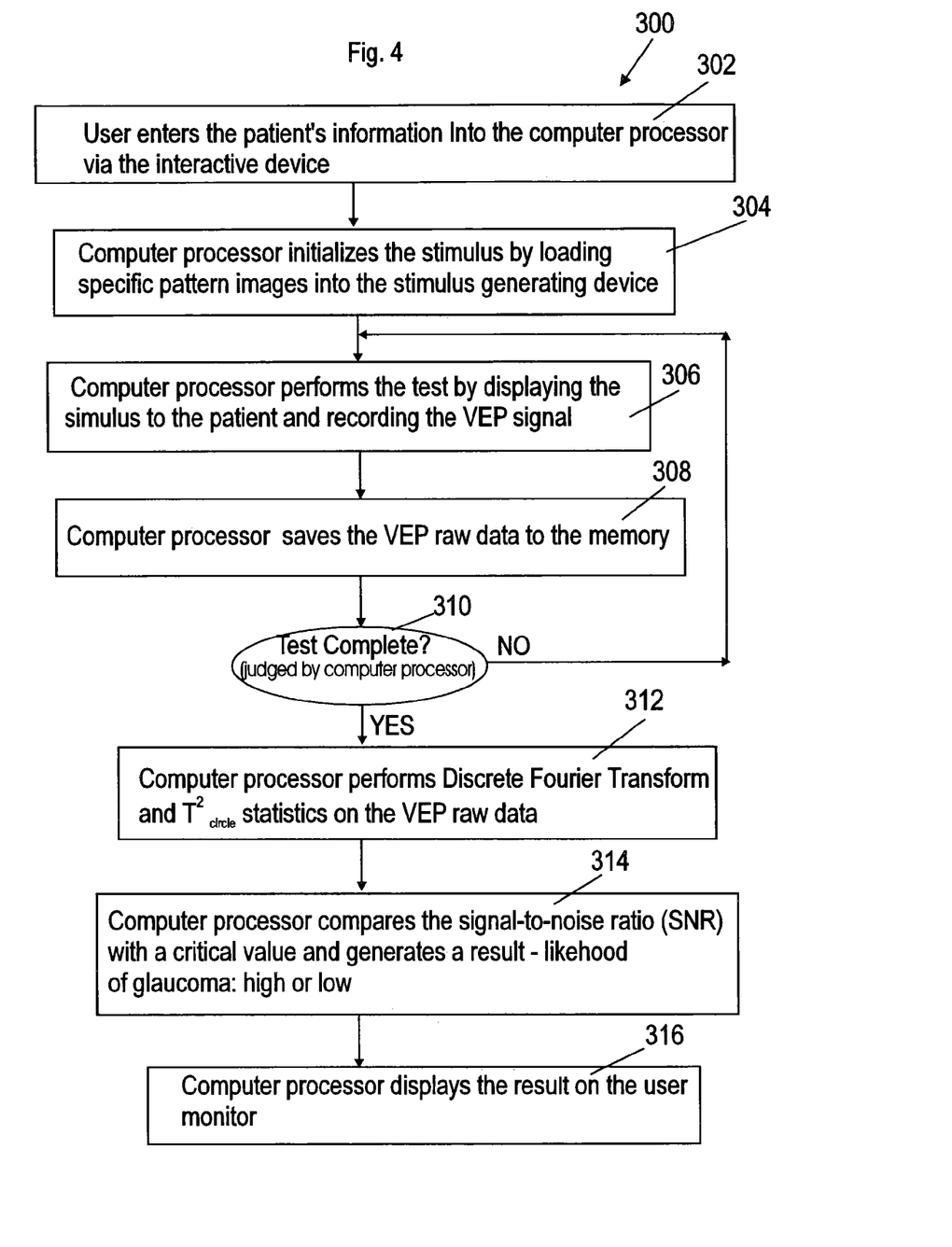
FIG. 4 shows a flow chart of a method in accordance with an embodiment of the current invention for evaluation of neural deficits in glaucoma suspects and patients.

FIG. 4 shows a flow chart 300 of a method of one embodiment of the current invention with an automated procedure and a method for evaluation of neural deficits in glaucoma suspects and patients.

At step 302 a user enters a patient's information, such as information for patient 17, into computer processor 12 via the interactive device 22. At step 304 the computer processor 12 initializes a stimulus by loading specific pattern images 100, 110 into the stimulus-generating device 16. At step 306, the computer processor 12 performs a test by timely controlling the stimulus-generating device 16 and VEP recording and measuring device 14 to display the stimulus to the patient 17 and to record the VEP signal through the recording and measuring device 14. At step 308, the computer processor 12 saves the VEP raw data to the memory 24. At step 310 the computer processor 12 determines if the test is complete. If the answer is no, then the procedure goes back to step 306. If the answer is yes then the procedure next executes step 312. At step 312 the computer processor 12 performs a discrete Fourier transform and $T^2_{circle}$ statistics on the saved VEP raw data. At step 314, the computer processor 12 compares the signal-to-noise ratio (SNR) with a preset critical value and generates a result—likelihood of glaucoma: high or low. At step 316 the computer processor 12 displays the result—likelihood of glaucoma high or low, such as through a text message, on the computer monitor 20.

The present invention in one or more embodiments incorporates computer software contained in the computer processor 12 for displaying a graphical user interface (GUI) on the operator's monitor 20 upon initiation of a testing procedure. The GUI allows an operator to enter patient data into the computer processor 12 (via the interactive device 22) such as date of birth, identification number, etc. After the patient's date is entered into the system at step 302, the computer processor 12 will initialize the stimulus patterns by loading the images into the stimulus-generating device 16 at step 304. At step 306, the test will begin with the presentation of the visual stimulus on the stimulus display screen 16a for observation by the patient 17 and data recording by the recording and measuring device 14, both are timely controlled by the computer processor 12. The stimulus may be comprised of both of the two visual images 100 and 110 depicted in FIG. 2 that alternate with a frequency of about twelve Hertz. The stimulus will typically be displayed for about five seconds. A set of five to ten of these stimuli will typically be presented to the patient 17 for observation by each eye of the patient 17. At step 308 after each stimulus presentation is complete, the recording device 14 will relay the recorded data to the computer processor 12 for saving the data into the memory 24. After a complete set of stimuli is presented to one eye, it will be presented again to the other eye. The number of stimulus presentations completed/data epochs collected is compared by the software program to the preset number (five or ten) to determine if the test is complete at step 310. Information in regard to the electrophysiological signal recorded during each stimulus display will be presented on the operator's monitor to track the patient 17's neural activity. Upon completion of presentation of the visual stimuli by the stimulus-generating device 16 and VEP data recording by device 14, the digitized VEP signals input to the computer processor 12 from the VEP recording and measuring device 14 will be immediately processed by the computer processor 12, at step 312.

The Fourier component of the VEP (amplitude and phase values) at the fundamental (stimulus) frequency (~twelve Hertz) will be calculated by the computer processor 12. The mean Fourier component from the five to ten repeated samples obtained from stimulation of each eye will also be calculated. A multivariate statistical method ($T^2_{circle}$, Victor & Mast, 1991) is used to estimate noise at the driven fundamental frequency, i.e., determine a circular 95% confidence region around the mean response vector. This circular region represents the set of pairs of values (cosine, sine) that are expected to encompass the true response to the given stimulus in 95% of the tests. Thus, the radius of the circle is used to quantitatively estimate the noise level, and the circular region is referred to as the "error circle."

Figure 5:
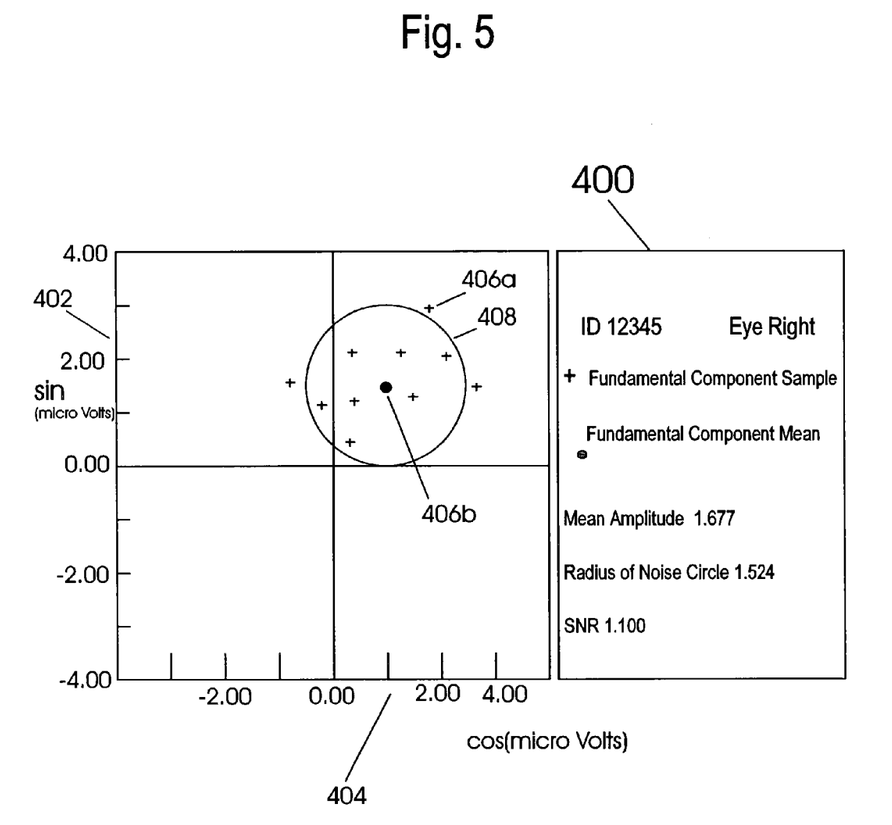
FIG. 5 demonstrates a test result for glaucoma assessment of an embodiment of the current invention for one eye.

In at least one embodiment of the current invention, the signal-to-noise ratio (SNR) is defined as the ratio of the mean amplitude of the fundamental Fourier component to the radius of the noise circle. FIG. 5 illustrates an example of a hypothetical test for one eye. The current system of one embodiment of the present invention will compare the SNR with a critical SNR value based on previous results from glaucoma research studies (e.g., Greenstein et al., 1998; Badr et al., 2003) to yield a decision—likelihood of glaucoma is high if the SNR is less than the critical value, or low if the SNR is equal to or greater than the critical value. The critical value may be a fixed value in one embodiment of the current invention (e.g., set to a value of 1). The current system of one embodiment of the present invention will display the status of the result for each eye tested on the computer monitor 20 immediately following the test done.

One aspect of the present invention is an apparatus that provides an objective, non-invasive and automated procedure for evaluation of early-stage glaucomatous damage. It integrates the following features: 1) novel stimulus technique, depicted in FIG. 2, that is designed to drive selectively the parallel pathway of interest (ON subdivision of the magnocellular pathway), which is known to be affected in the early stages of glaucomatous neuropathy; 2) discrete Fourier transform followed by application of the $T^2_{circle}$ statistical method; and 3) computerized technology. The automated procedure for VEP measurement and digital data processing together with a windows-based graphical user interface makes the machine easy to operate by non-expert users.

FIG. 5 demonstrates a chart 400 of test results for glaucoma diagnosis for one eye. The y-axis 402 is for the sine coefficient of the fundamental frequency component of the VEP obtained through Fourier analysis, and the x-axis 404 is for the corresponding cosine coefficient of this component. The "+" symbols, such as 406a are individual estimates of the fundamental component derived from each VEP epoch (five to ten epochs per test of each eye), the dot symbol 406b represents the mean of all of the fundamental component estimates such as 406a. The circle 408 represents the "error circle"—a 95% confidence region established with the $T^2_{circle}$ statistic.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

We claim:

1. A method for performing a medical test associated with glaucoma comprising
   displaying a plurality of visual stimuli for observation by one eye of a patient;
   detecting the patient's evoked brain potential signals in response to said stimuli through one or more electrodes attached to the patient's scalp;
   recording said evoked brain potential signals detected for each stimulus displayed:
   performing an automatic digital signal processing for a plurality of said recorded evoked brain potential signals following the recording;
   displaying an indication of whether there is a high or low likelihood of glaucoma on a computer monitor based on said digital signal processing; further wherein
   the digital signal processing comprises
      obtaining a plurality of fundamental frequency components of a plurality of the evoked brain potential signals corresponding to the periodic visual stimuli;
      performing a statistical method to determine a signal-to-noise ratio for said plurality of fundamental frequency components;
      comparing said signal-to-noise ratio with a preset critical value; and
      determining if the likelihood of glaucoma is high or low based on said comparison.

2. The method of claim 1 wherein
   the visual stimulus is comprised of two patterns, an isolated check pattern and a uniform field pattern, displayed alternately in a periodic manner at a frequency of about twelve Hertz.

3. The method of claim 1 wherein
   the recording comprises
      amplifying said evoked brain potential signals detected from said one or more electrodes attached to the patient's scalp;
      converting said evoked brain potential signals amplified from analog signals to digital signals.

4. The method of claim 1 further comprises
   an automated procedure for evoked brain potential signal recording and digital signal processing; wherein
      a computer processor controls both said evoked brain potential signal recording and said digital signal processing; and
      the computer processor initiates said digital signal processing immediately following the completion of said evoked brain potential signal recording.

5. The method of claim 1 further wherein
   the digital signal processing comprises
      performing a Discrete Fourier Transform on the plurality of the evoked brain potential signals recorded to obtain a plurality of fundamental frequency components of a plurality of the evoked brain potential signals corresponding to the periodic visual stimuli.

6. The method of claim 5 wherein
   the statistical method is a $T^2_{circle}$ method.

7. An apparatus for performing a medical test associated with glaucoma comprising a computer processor;

a visual stimulus generating device for presenting visual stimuli to a patient;

a visual evoked potential recording and measuring device;

a computer monitor; and a computer memory; wherein the computer processor is programmed by computer software residing in the computer memory to:

display a set of visual stimuli on said visual stimulus generating device for observation by a patient;

control said recording and measuring device to record a plurality of visual evoked potential signals in response to said set of visual stimuli detected from one or more electrodes attached to the patients scalp;

perform digital signal processing on the plurality of visual evoked potential signals recorded; and display an indication of whether there is a high or low likelihood of glaucoma on said computer monitor based on said digital signal processing; and further wherein the digital signal processing comprises obtaining a plurality of fundamental frequency components of a plurality of the evoked brain potential signals corresponding to the periodic visual stimuli;

performing a statistical method to determine a signal-to-noise ratio for said plurality of fundamental frequency components;

comparing said signal-to-noise ratio with a preset critical value; and determining if the likelihood of glaucoma is high or low based on said comparison.

8. The apparatus of claim 7 wherein
the visual stimulus generating device is comprised of a graphics card and a video monitor.

9. The apparatus of claim 7 wherein
the set of visual stimuli is comprised of an isolated check pattern and a uniform field pattern, displayed alternately in a periodic manner at a frequency of about twelve Hertz; and wherein the frequency and displaying alternately in a periodic manner is controlled by said computer software.

10. The apparatus of claim 7 wherein
the visual evoked potential recording and measuring device comprises an amplifier that enlarges the visual evoked potential signals detected from one or more electrodes attached to the patient's scalp;

an analog to digital converter that converts said amplified visual evoked potential signals to digital signals, and provides said digital signals to the computer processor; and wherein the analog to digital converter has a digital sampling rate that is controlled by said computer processor.

11. The apparatus of claim 7 further wherein
the digital signal processing comprises performing a Discrete Fourier Transform on the plurality of recorded visual evoked potential signals to obtain the plurality of fundamental frequency components of the plurality of the recorded visual evoked potential signals data corresponding to the periodic visual stimuli.

12. The apparatus of claim 11 wherein
the statistical method is a $T^2_{circle}$ method.

* * * * *